(12) United States Patent
Rubinsky et al.

(10) Patent No.: US 6,725,087 B1
(45) Date of Patent: Apr. 20, 2004

(54) METHOD AND APPARATUS FOR REMOTE IMAGING OF BIOLOGICAL TISSUE BY ELECTRICAL IMPEDANCE TOMOGRAPHY THROUGH A COMMUNICATIONS NETWORK

(75) Inventors: Boris Rubinsky, Albany, CA (US); David Otten, Berkeley, CA (US)

(73) Assignee: Telectroscan, Inc., Berkeley, CA (US)

( * ) Notice: Subject to any disclaimer, the term of this patent is extended or adjusted under 35 U.S.C. 154(b) by 189 days.

(21) Appl. No.: 09/664,026

(22) Filed: Sep. 19, 2000

(51) Int. Cl.[7] .................................................. A61B 5/05
(52) U.S. Cl. ........................... 600/547; 128/920; 705/3
(58) Field of Search ................................. 600/407, 547, 600/300; 128/920, 904; 705/3; 707/10

(56) References Cited

U.S. PATENT DOCUMENTS

| | | | |
|---|---|---|---|
| 4,486,835 A | * 12/1984 | Bai et al. ........................ | 378/21 |
| 5,544,662 A | * 8/1996 | Saulnier et al. ............. | 600/547 |
| 5,851,186 A | 12/1998 | Wood et al. | |
| 5,919,142 A | * 7/1999 | Boone et al. ................ | 600/547 |
| 6,006,191 A | 12/1999 | DiRienzo | |
| 6,044,131 A | 3/2000 | McEvoy et al. | |
| 6,201,990 B1 | * 3/2001 | Wexler et al. .............. | 600/547 |

* cited by examiner

Primary Examiner—Shawna J Shaw
(74) Attorney, Agent, or Firm—Lott & Friedland, P.A.

(57) ABSTRACT

A method and apparatus for imaging the internal structure of biological tissue from a remote location using electrical impedance tomography. The method and apparatus accomplish this by separating the functions of data acquisition from those of processing and imaging, and by connecting the data acquisition, processing and imaging components through a communications network, thus permitting the data acquisition, processing and imaging functions to be carried out at disparate locations within said network.

16 Claims, 5 Drawing Sheets

METHOD AND APPARATUS FOR REMOTE IMAGING OF BIOLOGICAL TISSUE BY ELECTRICAL IMPEDANCE TOMOGRAPHY THROUGH A COMMUNICATIONS NETWORK

TECHNICAL FIELD

The present invention relates generally to a method and apparatus for imaging the internal structure of biological tissue through the technique of electrical impedance tomography ("EIT"), and this invention specifically relates to a method and apparatus for remotely imaging the internal structure of biological tissue by acquiring raw data, transmitting same to a remote computer through a communications network, processing the raw EIT data at the remote computer and displaying an image of the internal structure of the biological tissue at said remote computer, at the location of data acquisition or at any other location.

BACKGROUND OF THE INVENTION

In the fields of medical diagnosis and research it is often necessary to visualize the internal tissue structures of biological subjects or patients which cannot be otherwise observed without invasive procedures. An example of an area where such visualization is helpful is in the detection, monitoring and analysis of tumors and other malignancies hidden inside the soft tissue of a subject or patient. When dealing with live subjects or patients it is usually not medically advisable or preferable to conduct an invasive procedure for diagnostic purposes unless there exists some prior indication that a particular feature, such as a tumor, is present in the tissue to be examined. In addition, even where there is knowledge or suspicion that a target feature exists, such a feature is sometimes located in an area which either cannot be reached through invasive procedures or would expose the subject or patient to undue medical risk should an invasive procedure be attempted. Moreover, invasive procedures expose subjects and patients to more generalized risks such as infection, bleeding, and other complications, which are not present with non-invasive visualization techniques. Finally, invasive procedures are almost invariably significantly more expensive and time-consuming than non invasive procedures.

Several non-invasive procedures have been developed to aid in the monitoring and visualization of internal structures found in biological tissue. Examples of such techniques are x-rays, ultrasound imaging, magnetic resonance imaging ("MRI"), computerized tomography ("CT"), and positron emission tomography ("PET.") Another such imaging technique, the technique to which the subject invention is directed to, is electrical impedance tomography ("EIT.") EIT relies on differences in bio-electrical properties within the target tissue to characterize different regions within it and subsequently output an image correlating to such characterization. Generally, an EIT scan is performed by placing a series of electrodes in a predetermined configuration in electrical contact with the tissue to be imaged. A low level electrical sinusoidal current is injected through one or more of the electrodes and a resulting voltage is measured at the remaining electrodes. This process may be repeated using different input electrodes, and electrical currents of different frequencies. By comparing the various input currents with their corresponding resulting voltages, a map of the electrical impedance characteristics of the interior regions of the tissue being studied can be imaged. It is also possible to map the impedance characteristics of the tissue by imposing a voltage and measuring a resulting current or by injecting and measuring combinations of voltages and currents. By correlating the impedance map obtained through an EIT scan with known impedance values for different types of tissues and structures, discrete regions in the resulting image can be identified as particular types of tissue (i.e., malignant tumors, muscle, fat, etc.)

Each of the above-mentioned imaging techniques has relative advantages and disadvantages, including varying abilities to image different types of tissue and structures at differing resolutions and different speeds. All modem imaging implementations, however, share one basic characteristic: they require equipment which is large, expensive and largely non-mobile, making it necessary for the subject or patient to be transported to a facility which houses the imaging equipment in order to have access to it.

For many reasons, some of which are herein detailed, it is desirable to be able to perform an EIT scan of a patient at a remote location, generate an image at a different location, and transmit the image back to the patient's location or to a physician or technician who may be located at yet a third site. In almost all situations, it is impractical from both an economic and logistical standpoint to transport current imaging equipment to a remote site where it is more convenient for the subject or patient for the imaging to be performed. Also, on occasion, it is impossible, due to health of the patient or subject and for other reasons, to transport the subject or patient to the facility housing the imaging equipment making it altogether impossible to perform imaging using currently available equipment and techniques. In addition, in some regions of the world there is very limited access, if any, to advanced imaging equipment, such as EIT, and to qualified physicians and/or technicians who can interpret the results of a diagnostic scan. For patients located in such regions it is impossible to receive the benefits of this type of diagnostic tool using existing equipment. Finally, the ability to perform EIT scans remotely, process images locally, and transmit resulting images to patients, technicians and/or physicians, carries the additional benefit of permitting a single server to operate as a central processing location for multiple scanning locations scattered anywhere within range of the communications network used to transmit data and images between the server and remote locations. Because the scanning equipment used for EIT imaging is relatively inexpensive in comparison with the image processing and generation equipment, the ability to service multiple scanners using one server has the potential to generate tremendous cost savings and efficiency gains.

Previous attempts have been made to provide remote capabilities to equipment used for imaging of biological tissue and structures such as described in U.S. Pat. No. 6,044,131 to McEvoy et al. ('131 patent); U.S. Pat. No. 6,006,191 to DiRienzo ('191 patent) and U.S. Pat. No. 5,851,186 to Wood et al. ('186 patent); all of which are incorporated herein by reference.

The '131 patent describes a security system for capture of x-ray images to a digital cassette which can download the images to a computer and assign them electronic signatures. The computer, in turn, can be directly connected to other computers via a modem or to a digital network of computers via a private communications link. Images on this system are accessible from remote locations by those who have proper authentication codes and have computers which have access to the private communications link. Although this system allows for electronic distribution of images to remote locations, x-ray systems such as this one inherently rely on large, expensive and non-mobile equipment to scan the subject or patient and to process the scanned data once it is digitized. As a result, this invention does not solve the problems associated with requiring a subject or patient to travel to a fixed location to be scanned. Moreover, because this system does not separate the data acquisition and processing functions, it is not possible to achieve the economic benefits of using a centralized data processing component to service multiple data acquisition components. Finally, the invention described by the '131 patent is limited to x-ray imaging which is not as effective as EIT in visualizing muscle and other soft tissues. Accordingly, the invention described in the '131 patent does not address or overcome the above-listed problems with existing imaging techniques.

The '191 patent describes a system for transmitting, storing, retransmitting and receiving electronic medical images and permits more efficient diagnostic readings by physicians during periods of down time. The system described by this patent is used to decentralize storage and distribution of electronic medical images and to direct images, such as x-rays, MRI, CT Scans, etc., which need interpretation, to medical professionals who read the images and diagnose conditions based on their readings. To accomplish this, the invention outlines methods for storage of medical images in digital format as well as a system that allows qualified physicians to bid on the opportunity to read and interpret stored images. The '191 patent, however, is directed only at remote access and distribution of medical images and not at remote creation of medical images. In order to input images into the system, the patient must rely on traditional imaging techniques which require them to travel to a facility that houses imaging equipment. Accordingly, the invention described in the '191 patent does not address or overcome the above-listed problems with existing imaging techniques.

The '186 patent describes a medical ultrasonic diagnostic imaging system which is capable of being accessed over data communication networks such as the Internet. The system described by the '186 patent allows a person to control an ultrasound imaging machine remotely over the Internet and to retrieve images from the ultrasound imaging machine. However, the remote capabilities of this invention are limited to controlling the ultrasound equipment and downloading of images. As with all other traditional imaging techniques previously described, the data acquisition (i.e., scanning) and processing of data both occur at the same location. Consequently, the equipment needed to perform these functions is bulky and expensive foreclosing the possibility of home use or use at locations where economic conditions make owning such equipment prohibitive. Moreover, although the '186 patent describes a networked embodiment of the invention in which multiple ultrasound imaging machines are linked and are remotely accessible, because the data acquisition and data processing functions are both performed locally, the equipment needed for such functions must be duplicated at every node of the network thus eliminating any cost savings. Accordingly, the invention described in the '186 patent does not address or overcome the above-listed problems with existing imaging techniques.

None of the inventions mentioned above describe a method or apparatus for remotely imaging the internal structure of biological tissue by acquiring raw data, transmitting same to a remote computer through a communications network, processing the raw EIT data at the remote computer and displaying an image of the internal structure of the biological tissue at said remote computer, at the location of data acquisition or at any other location.

Consequently, there is a need in the art for a method and apparatus which makes it possible to perform EIT imaging of biological tissue at a remote site without requiring the patient or subject to travel to a fixed location.

There is a further need in the art for a method and apparatus which allows patients to perform EIT imaging on themselves, in the privacy of their homes, without necessity of the services of a doctor or specialized medical technician.

There is a further need in the art for a method and apparatus which permits a doctor or medical technician to review and interpret EIT images of a patient located in one remote location, from a second remote location.

There is a further need in the art for a method and apparatus which makes it possible for a single image processing and generation server to centrally service multiple scanning locations within range of the communications network used to transmit data and images between the server and the remote scanning locations.

There is a further need in the art for a method and apparatus which for broadcasting to multiple locations, images generated locally from remote EIT scans of patients or subjects.

Finally, there is yet a further need in the art for a method of selling to patients, insurers, employers and other entities, remote EIT images and interpretation services thereof by qualified physicians and technicians.

SUMMARY OF THE INVENTION

The present invention overcomes significant deficiencies in the art by providing a method and apparatus for remotely imaging the internal structure of biological tissue from a remote location using electrical impedance tomography. The method and apparatus which is the subject of this invention accomplishes this by separating the functions of data acquisition from those of processing and imaging, and by connecting the data acquisition, processing and imaging components through a communications network, thus permitting the data acquisition, processing and imaging functions to be carried out at disparate locations within said network.

Generally described, the present invention describes an apparatus for remotely imaging the internal structure of biological tissue using the technique of electrical impedance tomography (EIT), comprising at least two electrodes arranged in a predetermined configuration electrically connected to the tissue, a power source for applying electrical input currents, voltages, or combinations thereof, of predetermined values to at least one of the electrodes, electrical measuring hardware for measuring the values of resulting output currents, voltages, or combinations thereof, at one or more of the electrodes, optionally, computer programming for converting the values of the electrical input currents, voltages, or combinations thereof and the values of the resulting output currents, voltages, or combinations thereof, into a format suitable for transmission over a communications network, communications hardware and software for transmitting the values of the electrical input currents, voltages, or combinations thereof, and the values of the resulting output currents, voltages, or combinations thereof, to a remote computer through a communications network, computer programming for calculating at the remote computer an electrical impedance value at one or more points on the tissue by analyzing the values of the electrical input currents, voltages, or combinations thereof, and the values of the resulting output currents, voltages, or combinations thereof using a front tracking or a hybrid algorithm, computer programming for generating an image of the internal structures of the tissue corresponding to the calculated impedance value or values, computer programming for transmitting from the remote computer through the communications network the image of the internal structures of the tissue to the location of the remote computer or to a location other than that of the remote computer; and computer programming and a monitor for displaying the image at the location of the remote computer or at the other location.

The present invention also describes, in general terms, a method for remotely imaging the internal structure of biological tissue using the technique of electrical impedance tomography (EIT), comprising the steps of electrically connecting at least two electrodes to the tissue, applying electrical input currents, voltages, or combinations thereof, of predetermined values to at least one of the electrodes, measuring the values of resulting output currents, voltages, or combinations thereof, at one or more of the electrodes, optionally converting the values of the electrical input currents, voltages, or combinations thereof and the values of the resulting output currents, voltages, or combinations thereof, into a format suitable for transmission over a communications network, transmitting the values of the electrical input currents, voltages, or combinations thereof, and the values of the resulting output currents, voltages, or combinations thereof, to a remote computer through the communications network, calculating at the remote computer an electrical impedance value at one or more points on the tissue by analyzing said values of the electrical input currents, voltages, or combinations thereof, and the values of the resulting output currents, voltages, or combinations thereof using a front tracking or a hybrid algorithm, generating an image of the internal structures of the tissue corresponding to the calculated impedance value or values, transmitting through the communications network the image of the internal structures of the tissue to the remote compute or to a location other than that of the remote computer; and displaying the image at the remote computer or other location.

In the preferred embodiment, the connecting step includes placing in direct proximity to the tissue to be examined, a probe of known dimensions, with at least two electrodes incorporated therein, so as to cause the electrodes to come in electrical contact with the tissue. The probe can be formed from rigid or flexible materials such that it is shaped to fit the particular geometrical features of the tissue to be studied.

In the preferred embodiment, the electrical input application step includes the designation of one of the electrodes on the probe as the source, or positive, electrode and a second electrode as the sink, or negative, electrode. The remaining electrodes are designated as differential electrodes. An input current, voltage, or combination thereof, of known value is applied by connecting a power source across the source and sink electrode pair, causing an electrical current to flow between the source and sink electrodes. Alternatively, if the probe incorporates only two electrodes, the second electrode would be designated as a differential electrode and the tissue would be directly connected to an electrical ground to complete the circuit. In addition to this, a number of different electrode injection and measurement configurations not mentioned here but well known in the art may be employed in the preferred embodiment.

In the preferred embodiment, the output measurement step includes using electrical measuring hardware to measure the output electrical current voltage or combination thereof which results from the electrical input at each of the differential electrodes.

In the preferred embodiment, the conversion step includes reducing, through techniques known in the relevant art, raw waveform values of measured output current, voltage, or combination thereof at each of the differential electrodes and input current voltage, or combination thereof, at the source and sink electrodes, into amplitude ratio and phase shift data which is more easily transmitted over a communications network. In an alternate embodiment of the present invention, the conversion step may be omitted and the measured raw waveforms may be transmitted without conversion.

In the preferred embodiment, the input application, output measurement and conversion steps are repeated several times using successive combinations of pairs of electrodes on the probe as the source and sink. The digital data resulting from each iteration of this process is stored until all data necessary for the desired imaging is acquired.

In the preferred embodiment, the transmitting step includes initially establishing communication with a remote computer containing software and hardware specifically programmed to receive the data generated in the previous steps. Once communication has been established, the data is transmitted to the remote computer where it is stored for processing. Communication with the remote computer is usually accomplished through the Internet. However, any type of communications network is acceptable to accomplish this step.

In the preferred embodiment, the calculation step includes initially accessing the data stored in the remote computer and demodulating the converted input and output values to recover the phase and amplitude information from the waveform data. Once the data is demodulated, it is processed using a reconstruction algorithm which calculates electrical impedance values at different points on the tissue and assigns a representative color to each point on the tissue depending on its impedance value. The output of this step is a three-dimensional numerical mapping of the subject tissue which designates an impedance value and corresponding color for different points in the tissue.

In the preferred embodiment, the display step includes creating a computer-readable graphical representation of the internal structures of the tissue in question from the numerical impedance mapping generated through the EIT scanning operation. The graphical representation can be stored, displayed on a monitor or printed at the location of the remote computer, or transmitted back to the location of the user or a third party, such as a physician or technician, for viewing, printing and/or storage.

Accordingly, it is an object of the present invention to provide a method and apparatus which makes it possible to perform EIT imaging of biological tissue at a remote site without requiring the patient or subject to travel to a fixed location.

Another object of the present invention is to allow patients to perform EIT imaging on themselves, in the privacy of their homes, without necessity of the services of a doctor or specialized medical technician.

Another object of the present invention is to permit a doctor or medical technician to review and interpret EIT images of a patient located in one remote location, from a second remote location.

Another object of the present invention is to provide a method and apparatus which makes it possible for a single image processing and generation server to centrally service multiple scanning locations within range of the communications network used to transmit data and images between the server and the remote scanning locations.

Another object of the present invention is to provide a method and apparatus for broadcasting to multiple locations, images generated locally from remote EIT scans of patients or subjects.

Another object of the present invention is to provide a method of selling to patients, insurers, employers and other entities, remote EIT images and interpretation services thereof by qualified physicians and technicians.

These and other objects, features and advantages of the present invention may be more clearly understood and appreciated from a review of the following detailed description of the disclosed embodiments and by reference to the appended drawings and claims.

DETAILED DESCRIPTION OF THE PREFERRED EMBODIMENT

Figure 1:
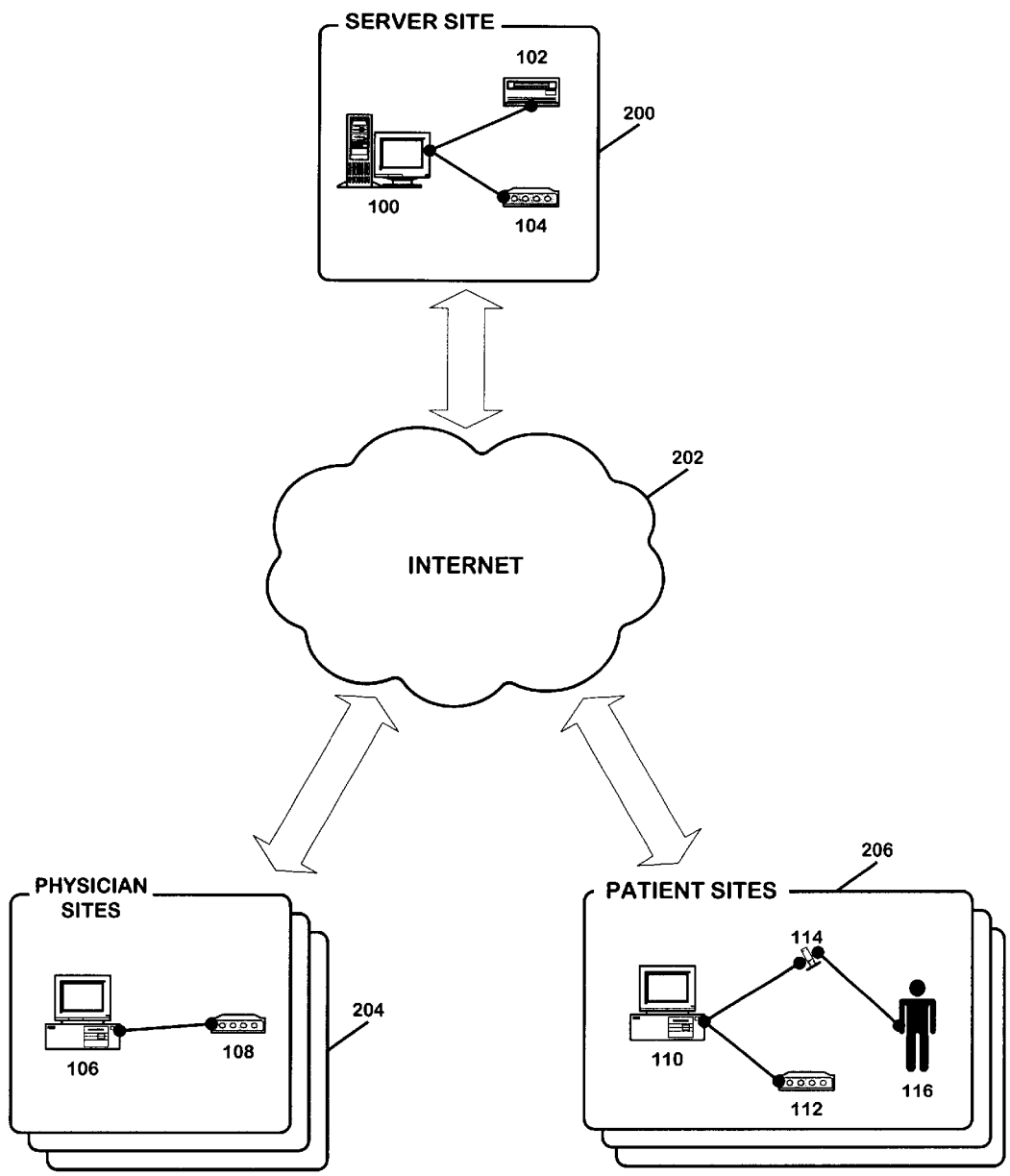
FIG. 1 is a schematic diagram illustrating the computer environment for practicing a preferred embodiment of the present invention.

Referring initially to FIG. 1 of the drawings, in which like numerals indicate like elements throughout the several views, the computer environment in a preferred embodiment of the present invention includes a server site 200 which is connected through the Internet 202 to one or more patient sites 206 and one or more physician sites 204. The communications link between the server site 200 and each of the patient sites 206 and physician sites 204 is bidirectional. The server site is equipped with a computer server 100, an electronic storage system 102 and a modem 104 or other communication device capable of connecting to the Internet. Each physician site is equipped with a personal computer 106 capable of connecting to the Internet through a modem 108 or other communication device. The patient sites are also equipped with a personal computer 110 capable of connecting to the Internet through a modem 112 or other communication device. In addition, each patient site is equipped with an electrode probe 114 which is connected to the site's personal computer 110 and is installed on the patient 116 at the location in the body where the imaging is to take place. The electrode probe 114 may be made of pliable material capable of conforming to different parts of the body or may be made of a rigid material depending on the part of the body which is to be imaged. The electrode probe 114 may also take the shape of a wearable garment, such as a woman's brassiere in a mammography application, in order to make it easier and more accurate to don and use.

Figure 2A:
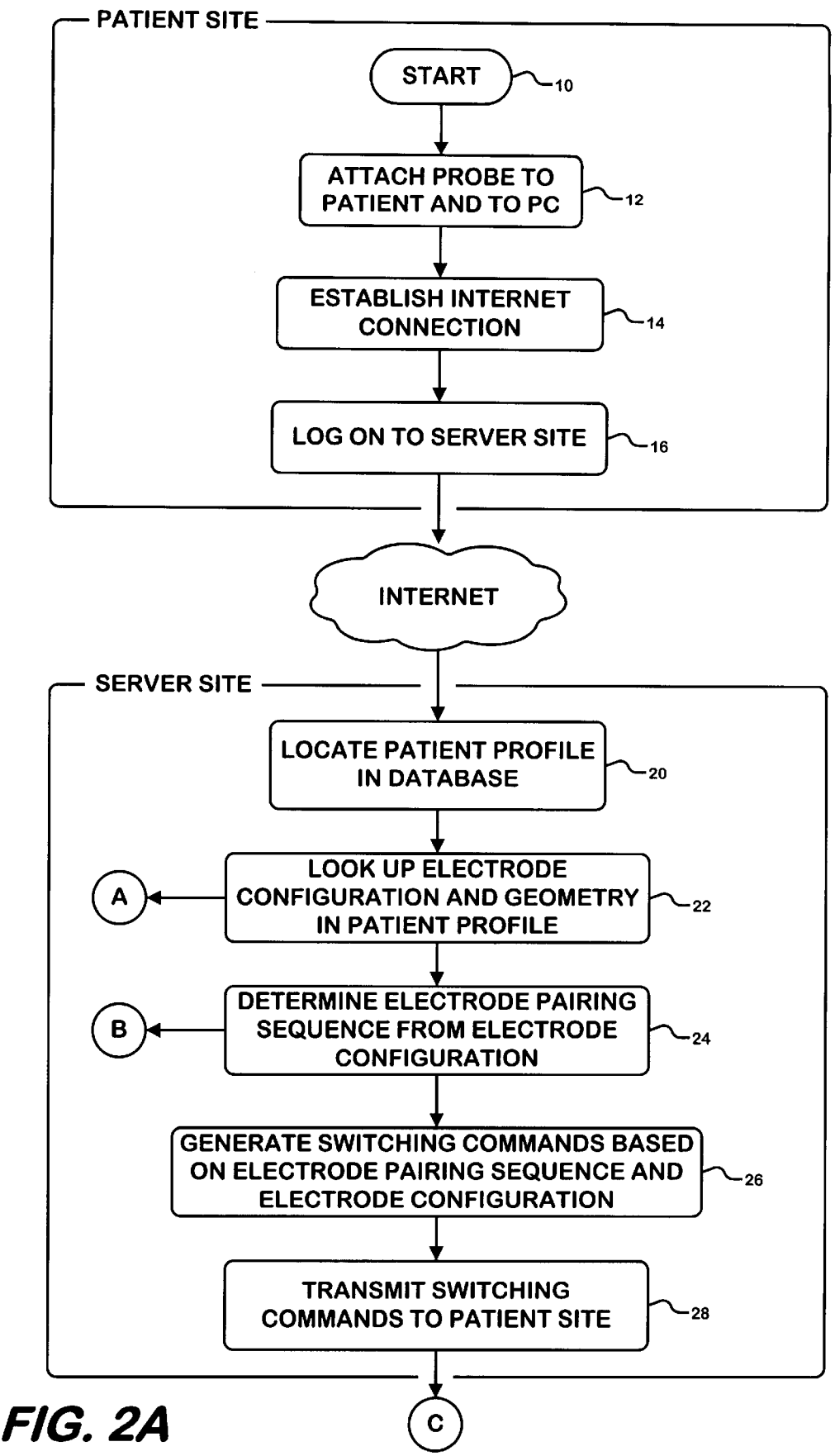
FIGS. 2A through 2D are a flowchart illustrating the steps in a system implementing a preferred embodiment of the present invention.

A flowchart depicting the steps involved in the typical application of a preferred embodiment of the present invention begins at FIG. 2A. The sequence begins at step 10 and advances to step 12 where the user, who may also be the patient, located at the patient site, attaches the electrode probe, which is connected to the personal computer at the site, to the part of the patient's body which is to be imaged. Next, in step 14 the user establishes an Internet connection to the server site and in step 16 logs on to the server by providing information such as a user name and password. If the correct log-on information is entered by the user, the sequence proceeds to step 20 where a patient profile record is located in a patient database accessible by the server. In step 22, the method then extracts from the patient profile record information regarding the electrode configuration and geometry for the probe attached to the patient in step 12. Alternatively, the information to be extracted from the patient profile record may be interactively input by the patient after log-on is accomplished. In step 24, using the electrode configuration and geometry, the server determines the electrode pairing sequence which is to be employed by the probe to acquire data from the patient. The electrode pairing sequence determines which of the probe's electrodes will act as the source, sink, reference and differential electrodes for each iteration in the data acquisition cycle. Based on the electrode geometry and the electrode pairing sequence, the server, in step 26, generates a series of switching commands which will be issued to current transmission hardware contained within the probe at the patient site. The switching commands are then transmitted in step 28 to the patient site.

Figure 2B:
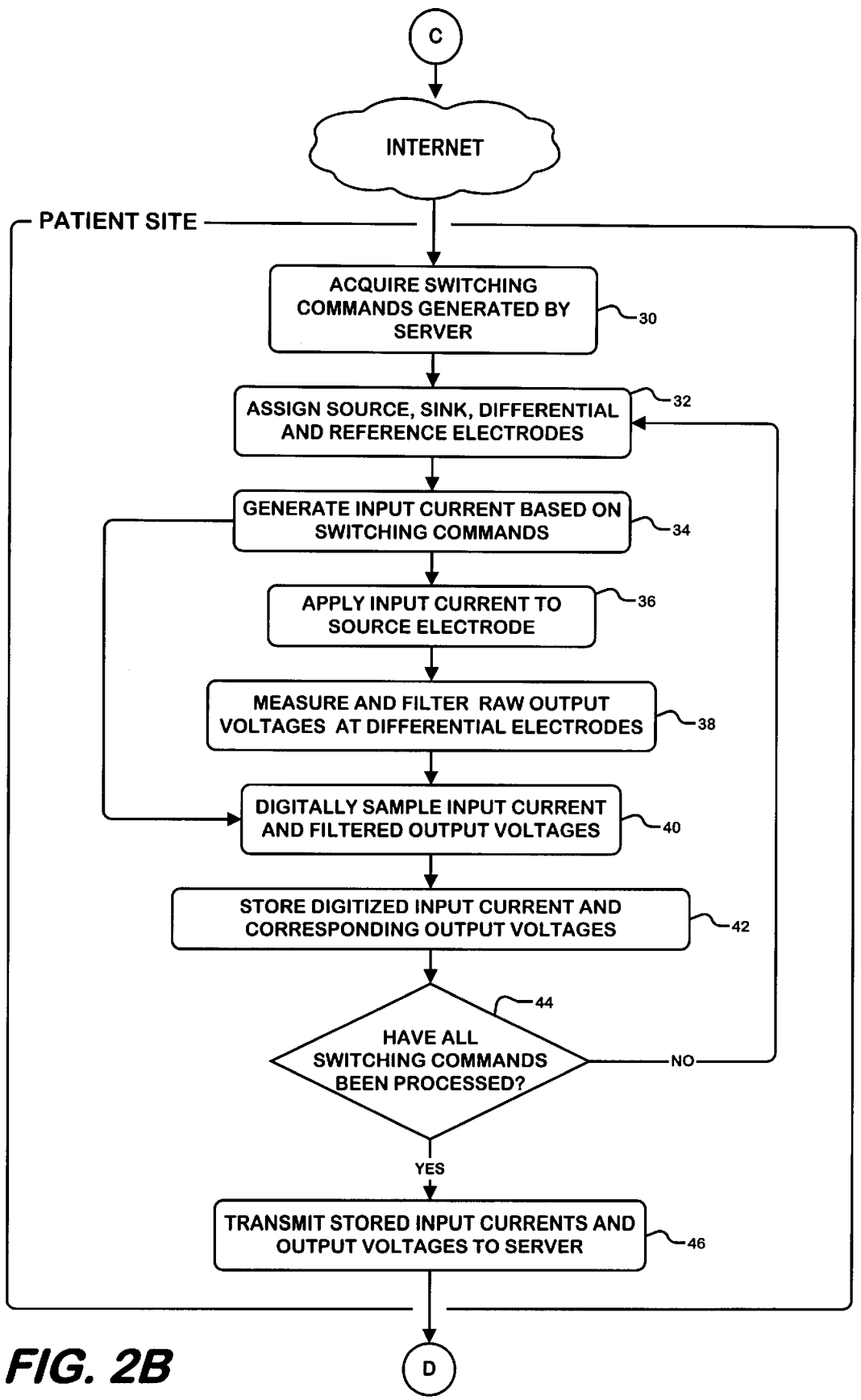

Turning to FIG. 2B, in step 30, at the patient site, the switching commands generated by the server are acquired by the current transmission hardware in the probe which in turn, in step 32, assigns the source, sink, differential and reference electrodes within the probe for the first iteration of the data acquisition cycle. In step 34, the current transmission hardware generates an input current or voltage based on the switching commands which is then applied to the source electrode in step 36. In step 38, a resulting output current or voltage is measured at each of the differential electrodes and is filtered to remove electrical noise. The output signal measured and filtered in step 38 and the input signal generated in step 34 are digitally sampled in step 40. The sampling process entails observing the analog current and voltage signals at each electrode over a prescribed period of time and recording a numerical value in digital format which corresponds to the voltage level at each electrode at fractional increments in time over said prescribed period of time. Next, in step 42, the digital input signal value and its corresponding digital output signal values are stored in memory. The sequence then advances to step 44 where a query is made to determine if all of the switching commands transmitted to the patient site have been processed. If the answer to this query is "No," then steps 32 through 42 are repeated for the next switching command in the sequence. This process is repeated until all switching commands have been processed and multiple sets of digital input signal values and digital output signal values are stored in memory. Once the last switching command has been processed, the answer to the query in step 44 will be "Yes" and the method continues to step 46 where the stored digital input signal values and digital output signal values are transmitted to the server site for processing.

Figure 2C:
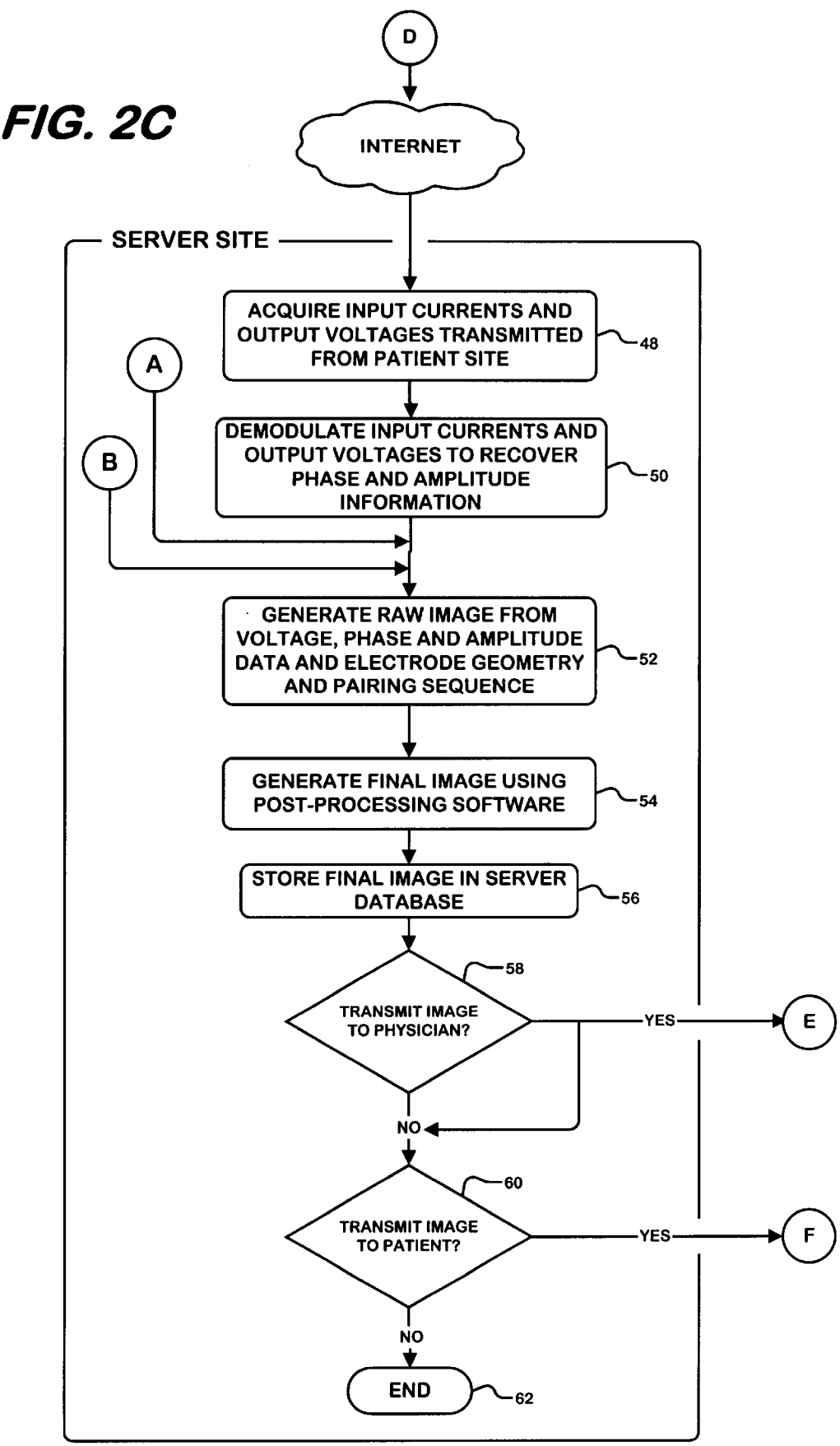

Turning next to FIG. 2C, in step 48 the digital input signal values and digital output signal values are received by the server which, in turn, in step 50 demodulates the values to recover amplitude and phase information from the digital sampling process of step 40. In step 52, using the phase and amplitude data from step 50, the electrode geometry determined in step 22 and the electrode pairing sequence determined in step 24, the server generates a raw image which corresponds to a three dimensional color mapping of impedance values for multiple adjacent points located in the part of the patient's body to which the electrode probe is attached. In order to generate the raw image, the server uses a specialized reconstruction algorithm which is based on a front tracking technique developed especially for use with the present invention. Use of the front tracking technique allows generation of a high-resolution image using significantly fewer independent voltage measurements and electrodes resulting in substantial time and resource savings.

Details of the front tracking reconstruction algorithm are discussed in detail below.

Continuing with step 54, the raw image is filtered by post-processing software to remove noise and to sharpen details and a final image is generated. Then, in step 56, the final image is stored at the server and linked to the patient's profile in the patient database. In step 58, the method queries to determine whether a copy of the final image should be transmitted to a physician site for interpretation. If the answer to the query is "Yes", the final image is transmitted to the physician site before continuing to step 60. The Internet address for the physician site to which the image is transmitted is obtained from the patient's profile. If the answer is "No," the method continues to step 60 without transmitting the final image to the physician site. In step 60, another query is made to determine whether a copy of the final image should be sent to the patient site. If the answer is "No," the method terminates at the server site at step 62. If the answer is "Yes," a copy of the final image is transmitted to the patient site.

Figure 2D:
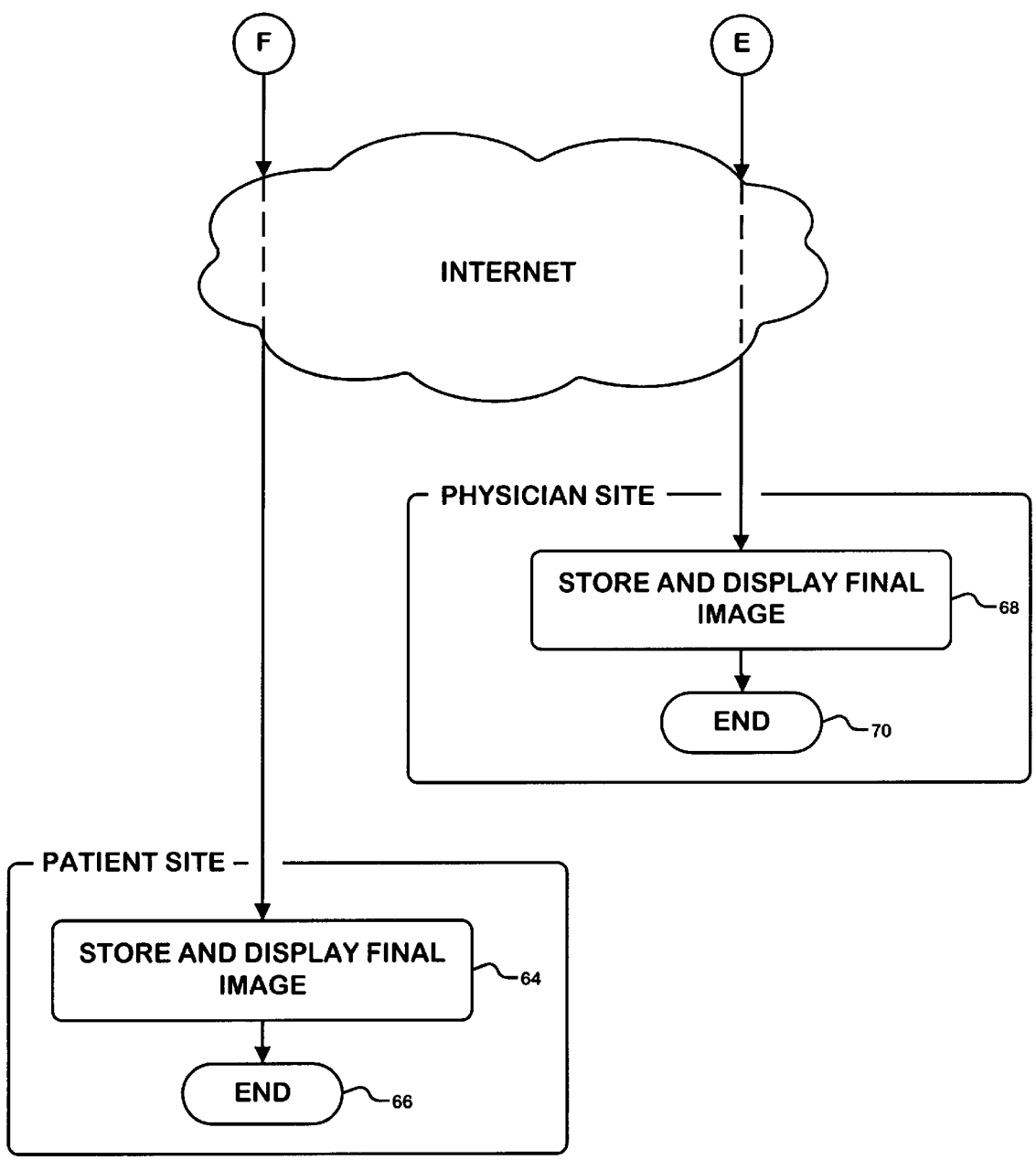

Turning finally to FIG. 2D, once an image has been transmitted to a patient site, in step 64, the image is stored and displayed at the personal computer in the patient site. Execution then terminates at the patient site in step 66. Similarly, once an image has been transmitted to a physician site, in step 68, the image is stored and displayed at the personal computer in the physician site. Execution then terminates at the physician site in step 70.

It will be evident from the foregoing that modifications of the EIT method and apparatus herein described can be effected without departing from the principles of the invention. For example, in addition to physician interpretation of images generated using the present invention, it is also possible for the server to automatically compare multiple images of the same patient taken over time and to alert the patient or a designated physician to a particular course of action based on changes in the images.

Front Tracking Reconstruction Algorithm

The central role of an EIT image reconstruction algorithm is to determine the impedance distribution within a region of interest given a set of current-induced voltage measurements taken at the region's surface (either internal or external). One of the most reliable reconstruction techniques is known as the Newton-Raphson method, a general description of which follows. First, a region of interest within the body is identified and geometrically defined. A pattern of electrode placements suitable to this region is then determined, and the absolute electrode positions are measured. Accompanying this electrode arrangement is the data collection algorithm which defines the ordering of the current source/sink and voltage measurement electrode pairs during an image scan. Decisions involving the electrode geometry and data collection algorithm are based upon the imaging region geometry and the specific application, and will ultimately determine the overall attainable image quality.

These pre-procedure definitions are then used to create a mathematical model representing the real imaging region of interest. The model is designed to reflect all relevant bioelectrical physical behavior expected of the real imaging region. That is to say, if the exact impedance distribution of the real region were known, it could be entered into the model and be expected to produce the same voltage measurements as the real system given identical electrode placement and data collection algorithms. This model may then be used as a testing tool for possible impedance distribution candidates by comparing the measured voltages from the real and model regions. The smaller the overall difference in voltage measurements between real and modeled systems, the more closely the modeled impedance distribution represents the real distribution.

Reconstructing an image then become an iterative process involving an initial distribution guess, a testing of that guess via comparison of modeled and real voltage measurements, and a refining of the initial guess based on the comparison results. This process is repeated until the real and modeled measurements are suitably close.

There are two major components of the Newton-Raphson technique: the modeling method, and guess refining algorithm. Most existing modeling methods take a finite element approach which will hereinafter be referred to as an impedance mapping technique. Briefly, this approach approximates a bioelectrical continuum as a set of connected electrically homogeneous elements with enforced boundary continuity. Each element represents an impedance "pixel". The more elements, the better the image resolution.

The modeling approach which is the subject of this invention differs fundamentally from this impedance mapping method, and will hereinafter be referred to interchangeably as the front tracking technique or front tracking method. The front tracking technique breaks the region of interest into a number of electrically homogeneous zones defined by a finite number of simply connected boundary segments. The placement of the segment endpoints then define the shape of each zone, with more segments allowing a finer shape resolution. The mathematical method of solution for this model description is known as the boundary element method.

The two things that characterize the type of guess refining algorithm used in the Newton-Raphson method are the parameters which are being refined, and the method of that refinement. Impedance mapping techniques adjust the impedance of each element, whereas the front tracking method adjusts the location of boundary segment endpoints, and therefore the shape of the electrically homogeneous zones. The method of refinement in each case is based on a differential matrix, or Jacobian calculation. This matrix represents the unit change in each measured voltage given a unit change in each element impedance (impedance mapping) or segment end position (front tracking).

One of the major advantages of front tracking over impedance mapping techniques is a drastic decrease in the necessary number of electrodes needed to produce comparable images. Inverse problems of this type are mathematically constrained in that they require at least as many independent voltage measurements as there are adjusting parameters (i.e. elemental impedances or segment end positions). Many imaging applications, such as localized cancers, have fairly simple geometries which can be described well by a small number of shape segments using front tracking. In contrast, impedance mapping would require a comparatively large number of elements, and therefore electrodes, to achieve similar morphological distinction. Front tracking also naturally enforces the expected step changes in impedance across tumor or organ boundaries. Impedance mapping algorithms tend to smooth these boundaries, degrading important morphology features.

One challenging aspect of the front tracking method not present in impedance mapping, is the need to "seed" electrically homogeneous zones. That is, before the front tracking algorithm can begin refining a given shape, it needs to know where, how many, and how big the initial zone guesses should be. A solution to this problem is achieved by combining aspects of the two reconstruction algorithms. A typical sequence demonstrating this would begin by using impedance mapping to roughly identify probable homogeneous zones within the region of interest. These areas would be seeded and the front tracking algorithm would take over in further refinement of each zone's shape until the overall difference between modeled and physical surface voltages was acceptable. Thus, by exploiting the specific strengths of each algorithm, a technique more effective than either the front tracking or impedance mapping technique alone is realized. This combined technique is hereinafter referred to as a hybrid technique.

It will be understood by those skilled in the relevant art that while the preferred embodiment is directed towards a system based on application of EIT technology, alternative imaging technologies could be utilized in carrying out the present invention, including, without limitation, x-rays, ultrasound imaging, magnetic resonance imaging ("MRI"), computerized tomography ("CT"), and positron emission tomography ("PET.")

Accordingly, it will be understood that the preferred embodiment of the present invention has been disclosed by way of example and that other modifications and alterations may occur to those skilled in the art without departing from the scope and spirit of the appended claims.

What is claimed is:

1. A method for remotely imaging internal structures of biological tissue using the technique of electrical impedance tomography (EIT), comprising the steps of:

electrically connecting at least two electrodes to said tissue;

applying electrical input currents, voltages, or combinations thereof, of predetermined values to at least one of said electrodes;

measuring the values of resulting output currents, voltages, or combinations thereof, at at least two of said electrodes;

transmitting said values of said electrical input currents, voltages, or combinations thereof, and said values of said resulting output currents, voltages, or combinations thereof, to a remote computer through a communications network;

calculating at said remote computer, utilizing a front tracking technique, an electrical impedance value at one or more points on said tissue by analyzing said values of said electrical input currents, voltages, or combinations thereof, and said values of said resulting output currents, voltages, or combinations thereof; and generating an image of internal structures of said tissue corresponding to said calculated impedance value or values.

2. The method of claim 1 further comprising the step of displaying said image of said internal structures of said tissue at the location of said remote computer.

3. The method of claim 1 further comprising the steps of:
   transmitting through said communications network said image of said internal structures of said tissue to a location other than that of said remote computer; and
   displaying said image at said other location.

4. The method of claim 1 wherein said calculating step is carried out by utilizing a hybrid technique comprising a combination of a front tracking technique and an impedance mapping technique.

5. The method of claim 1 further comprising after said measuring step and before said transmitting step the step of:
   converting said values of said electrical input currents, voltages, or combinations thereof and said values of said resulting output currents, voltages, or combinations thereof, into a format suitable for transmission over a communications network.

6. The method of claim 5 further comprising the step of displaying said image of said internal structures of said tissue at the location of said remote computer.

7. The method of claim 5 further comprising the steps of:
   transmitting through said communications network said image of said internal structures of said tissue to a location other than that of said remote computer; and
   displaying said image at said other location.

8. The method of claim 5 wherein said calculating step is carried out by utilizing a hybrid technique comprising a combination of a front tracking technique and an impedance mapping technique.

9. An apparatus for remotely imaging internal structures of biological tissue using the technique of electrical impedance tomography (EIT), comprising:

at least two electrodes arranged in a predetermined configuration adapted to be electrically connected to the tissue;

a power source for applying electrical input currents, voltages, or combinations thereof, of predetermined values to at least one of said electrodes;

electrical measuring hardware for measuring the values of resulting output currents, voltages, or combinations thereof, at at least two of said electrodes;

communications hardware and software for transmitting said values of said electrical input currents, voltages, or combinations thereof, and said values of said resulting output currents, voltages, or combinations thereof, to a remote computer through a communications network;

computer readable instructions for calculating at said remote computer, using a front tracking technique, an electrical impedance value at one or more points on said tissue by analyzing said values of said electrical input currents, voltages, or combinations thereof, and said values of said resulting output currents, voltages, or combinations thereof; and computer readable instructions for generating an image of an internal structure of said tissue corresponding to said calculated impedance value or values.

10. The apparatus of claim 9 further comprising computer software and a monitor for displaying said image of said internal structures of the tissue at the location of said remote computer.

11. The apparatus of claim 9 further comprising:
    computer readable instructions for transmitting from said remote computer through said communications network said image of said internal structures of the tissue to a location other than that of said remote computer; and
    computer readable instructions and a monitor for displaying said image at said other location.

12. The apparatus of claim 9 wherein said computer readable instructions for calculating at said remote computer an electrical impedance value at one or more points on the tissue implements a hybrid technique comprising a combination of a front tracking technique and an impedance mapping technique.

13. The apparatus of claim 9 further comprising:
    computer readable instructions for converting said values of said electrical input currents, voltages, or combinations thereof and said values of said resulting output currents, voltages, or combinations thereof, into a format suitable for transmission over a communications network.

14. The apparatus of claim 13 further comprising computer readable instructions and a monitor for displaying said image of said internal structures of the tissue at the location of said remote computer.

15. The apparatus of claim 13 further comprising:

computer readable instructions for transmitting from said remote computer through said communications network said image of said internal structures of the tissue to a location other than that of said remote computer; and computer readable instructions and a monitor for displaying said image at said other location.

16. The apparatus of claim 13 wherein said computer readable instructions for calculating at said remote computer an electrical impedance value at one or more points on the tissue implements a hybrid technique comprising a combination of a front tracking technique and an impedance mapping technique.

* * * * *